United States Patent
Khandkar

(10) Patent No.: US 9,452,115 B2
(45) Date of Patent: *Sep. 27, 2016

(54) RADIATION PROTECTION SYSTEM

(71) Applicant: BLOXR Solutions, LLC, Salt Lake City, UT (US)

(72) Inventor: Ashok C. Khandkar, Salt Lake City, UT (US)

(73) Assignee: BLOXR SOLUTIONS, LLC, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/799,298

(22) Filed: Jul. 14, 2015

(65) Prior Publication Data

US 2015/0313811 A1 Nov. 5, 2015

Related U.S. Application Data

(63) Continuation of application No. 12/683,727, filed on Jan. 7, 2010, now Pat. No. 9,114,121.

(51) Int. Cl.

| *A61K 33/24* | (2006.01) |
| --- | --- |
| *A61K 9/06* | (2006.01) |
| *A61K 9/107* | (2006.01) |
| *A61K 8/19* | (2006.01) |
| *A61B 6/10* | (2006.01) |
| *A61B 6/00* | (2006.01) |
| *A61Q 17/04* | (2006.01) |
| *A61K 9/00* | (2006.01) |

(52) U.S. Cl.
CPC ............ *A61K 8/19* (2013.01); *A61B 6/107* (2013.01); *A61B 6/485* (2013.01); *A61K 9/0014* (2013.01); *A61K 9/06* (2013.01); *A61K 33/24* (2013.01); *A61K 33/245* (2013.01); *A61Q 17/04* (2013.01); *A61K 2800/20* (2013.01)

(58) Field of Classification Search
None
See application file for complete search history.

(56) References Cited

U.S. PATENT DOCUMENTS

| 3,200,085 A | 8/1965 | Guglielmo |
| 3,200,087 A | 8/1965 | Robinson |
| 4,938,233 A * | 7/1990 | Orrison, Jr. ............ A61B 6/107 128/849 |
| 5,001,354 A | 3/1991 | Gould et al. |
| 5,059,807 A | 10/1991 | Kersten et al. |
| 5,245,195 A | 9/1993 | Shah et al. |
| 5,548,125 A | 8/1996 | Sandbank |
| 5,604,784 A | 2/1997 | Widlicka et al. |
| 6,232,383 B1 | 5/2001 | Joseph |
| 6,281,515 B1 | 8/2001 | Demeo et al. |
| 6,459,091 B1 | 10/2002 | Demeo et al. |
| 6,472,476 B1 | 10/2002 | Soane et al. |
| 6,517,933 B1 | 2/2003 | Soane et al. |
| 6,544,594 B2 | 4/2003 | Linford et al. |
| 6,674,087 B2 | 1/2004 | Cadwalader et al. |
| 6,855,772 B2 | 2/2005 | Linford et al. |
| 7,449,194 B2 | 11/2008 | Lelah et al. |
| 7,449,705 B2 | 11/2008 | Eder |
| 7,659,439 B2 | 2/2010 | Grossman |
| 8,067,758 B2 | 11/2011 | Popa-Simil et al. |
| 8,754,389 B2 | 6/2014 | Khandkar et al. |
| 8,993,989 B1 | 3/2015 | Khandkar et al. |
| 9,114,121 B2 * | 8/2015 | Khandkar ............ A61K 9/0014 |
| 2001/0022965 A1 | 9/2001 | Heger et al. |
| 2002/0148980 A1 | 10/2002 | Cadwalader et al. |
| 2003/0010939 A1 | 1/2003 | Demeo et al. |
| 2003/0095935 A1 | 5/2003 | Chaiyawat |
| 2004/0001894 A1 | 1/2004 | Leibowitz |
| 2004/0004196 A1 | 1/2004 | DeMeo et al. |
| 2004/0041104 A1 | 3/2004 | Cadwalader et al. |
| 2004/0041107 A1 | 3/2004 | Cadwalader et al. |
| 2004/0124374 A1 | 7/2004 | Joseph |
| 2004/0262546 A1 | 12/2004 | Thiess et al. |
| 2005/0211930 A1 * | 9/2005 | DeMeo ................. G01V 5/0008 250/516.1 |
| 2005/0256439 A1 | 11/2005 | Grossman |
| 2006/0038140 A1 | 2/2006 | Grilliot et al. |
| 2006/0151749 A1 | 7/2006 | Thiess et al. |
| 2006/0151750 A1 | 7/2006 | Eder |
| 2006/0210500 A1 | 9/2006 | Bicard-Benhamou et al. |
| 2007/0075277 A1 | 4/2007 | Smith et al. |
| 2008/0128658 A1 | 6/2008 | Jungermann et al. |
| 2008/0128660 A1 | 6/2008 | Thiess |
| 2008/0164425 A1 | 7/2008 | Cadwalader et al. |
| 2008/0182093 A1 | 7/2008 | Sonntag et al. |
| 2008/0249594 A1 | 10/2008 | Dietrich et al. |
| 2008/0272318 A1 | 11/2008 | Cadwalader et al. |

(Continued)

FOREIGN PATENT DOCUMENTS

| EP | 2058821 | 5/2009 |
| GB | 1491202 | 11/1977 |

(Continued)

OTHER PUBLICATIONS

Remington's Pharmaceutical Sciences (17th Ed. 1985), pp. 1301, 1303-1305, 1588.*

(Continued)

*Primary Examiner* — Abigail Fisher
*Assistant Examiner* — Frank Choi
(74) *Attorney, Agent, or Firm* — Stoel Rives LLP

(57) ABSTRACT

The present invention relates to a shield for radiation attenuation. The shield includes a carrier suitable for topical application on human tissue, such as skin. The carrier includes an active ingredient that is homogenously dispersed throughout the carrier. The active ingredient includes an element suitable for attenuating radiation and having a high atomic number.

17 Claims, 4 Drawing Sheets

(56) References Cited

U.S. PATENT DOCUMENTS

| | | |
|---|---|---|
| 2008/0296541 A1 | 12/2008 | Hamilton et al. |
| 2009/0027921 A1 | 1/2009 | Chou et al. |
| 2009/0078891 A1 | 3/2009 | Oyaizu |
| 2009/0198007 A1 | 8/2009 | Wang |
| 2009/0272921 A1 | 11/2009 | Ballsieper |
| 2010/0163758 A1 | 7/2010 | Kirschenbaum |
| 2010/0176317 A1 | 7/2010 | Smith |
| 2010/0186753 A1 | 7/2010 | Buckley |
| 2011/0163248 A1 | 7/2011 | Beck |
| 2011/0165269 A1 | 7/2011 | Khandkar |
| 2011/0165373 A1 | 7/2011 | Khandkar |
| 2012/0248346 A1 | 10/2012 | Chowdhary et al. |
| 2013/0079862 A1 | 3/2013 | Ellrich |
| 2013/0240763 A1 | 9/2013 | Khandkar et al. |
| 2014/0021377 A1 | 1/2014 | Khandkar et al. |
| 2014/0151584 A1 | 6/2014 | Khandkar et al. |
| 2014/0205860 A1 | 7/2014 | Khandkar |
| 2014/0212679 A1 | 7/2014 | Khandkar |
| 2015/0083941 A1 | 3/2015 | Khandkar et al. |

FOREIGN PATENT DOCUMENTS

| | | |
|---|---|---|
| JP | 06122803 | 5/1994 |
| JP | 11043326 | 2/1999 |
| JP | 2007085865 | 4/2007 |
| JP | 2007217361 A | 8/2007 |
| JP | 2008189576 | 8/2008 |
| WO | 2005049713 | 6/2005 |
| WO | 2006090629 | 8/2006 |
| WO | 2011085273 | 7/2011 |
| WO | 2012138565 | 10/2012 |
| WO | 2014088728 A3 | 6/2014 |

OTHER PUBLICATIONS

European Examination Report dated Feb. 18, 2016 for EP11732251l.
Extended European Search Report dated Aug. 23, 2013 for EP11732251.1.
International Preliminary Report on Patentability dated Jul. 10, 2012 for PCT/US2011/020608.
International Search Report and Written Opinion dated Mar. 11, 2011 for PCT/US2011/020608.
International Search Report and Written Opinion dated Jul. 20, 2012 for PCT/US2012/031489.
International Search Report and Written Opinion dated Sep. 2, 2014 for PCT/US2013/067333.
Kiran, "Lead Equivalence Test Procedure", Mar. 2014.
McCaffrey et al., "Optimizing Non-Pb Radiation Shielding Materials Using Bilayers", Med Phys 36(12), Dec. 2009.
McCaffrey et al., "Radiation Shielding Materials and Radiation Scatter Effects for Interventional Radiology (IR) Physicians", Med Phys 39(7), Jul. 2012.
Notice of Allowance dated Apr. 28, 2014 for U.S. Appl. No. 13/710,172.
Notice of Allowance dated May 19, 2015 for U.S. Appl. No. 12/683,727.
Notice of Allowance dated Dec. 19, 2014 for U.S. Appl. No. 14/305,887.
Office Action May 16, 2013 for U.S. Appl. No. 13/710,172.
Office Action dated Jan. 15, 2014 for U.S. Appl. No. 13/710,172.
Office Action dated Feb. 3, 2015 for U.S. Appl. No. 13/663,467.
Office Action dated Mar. 7, 2014 for U.S. Appl. No. 13/436,344.
Office Action dated Mar. 14, 2014 for U.S. Appl. No. 12/897,611.
Office Action dated Mar. 25, 2014 for U.S. Appl. No. 13/421,961.
Office Action dated Jun. 4, 2014 for U.S. Appl. No. 13/663,467.
Office Action dated Jun. 21, 2012 for U.S. Appl. No. 12/683,727.
Office Action dated Jun. 30, 2014 for U.S. Appl. No. 13/421,961.
Office Action dated Jul. 29, 2013 for U.S. Appl. No. 13/421,961.
Office Action dated Aug. 4, 2014 for U.S. Appl. No. 14/305,887.
Office Action dated Aug. 26, 2013 for U.S. Appl. No. 13/710,172.
Office Action dated Oct. 6, 2014 for U.S. Appl. No. 12/683,727.
Office Action dated Dec. 20, 2012 for U.S. Appl. No. 13/421,961.
Supplementary Partial European Search Report dated Aug. 14, 2013 for EP11732251.
Wu et al, "Realizing Visible-Light-Induced Self-Cleaning Property of Cotton Through Coating N-TiO2 Film and Loading AgI Particles", ACS Appl Mater Interfaces, 3(12), 2011, pp. 4770-4774.
Office Action dated Jul. 3, 2013 for U.S. Appl. No. 12/683,727.
Office Action dated Jul. 15, 2013 for U.S. Appl. No. 12/897,611.
Office Action dated Jul. 7, 2014 for U.S. Appl. No. 12/897,611.

* cited by examiner

RADIATION PROTECTION SYSTEM

CROSS-REFERENCE TO RELATED APPLICATIONS

This patent application is a continuation of U.S. patent application Ser. No. 12/683,727 entitled RADIATION PROTECTION SYSTEM, filed on Jan. 7, 2010, which is incorporated herein by reference in its entirety.

BACKGROUND OF THE INVENTION

1. Field of the Invention

The present invention relates to shielding systems for attenuating radiation energy from fluorescent imaging systems that employ radiation energy, especially for the protection of medical staff and patients against the damaging effects of x-rays and other similar high energy radiation used in surgical and other medical procedures.

2. The Relevant Technology

Physicians and allied clinical personnel, collectively referred to as medical staff, are commonly involved in medical procedures involving patients in which fluoroscopic and other types of radiation systems (such as computer tomography, or CT, systems) are used for purposes of diagnostic detection or guidance procedures. These radiation systems allow the medical staff to peer into the body systems of a patient with minimal invasiveness. The images generated may be in the form of a single image, or a video feed, both of which may be live. For example, the anatomy of a patient may be illuminated using x-rays so that the medical staff can carry out the procedures using a fluoroscopic viewing screen. In one case, x-ray fluoroscopy may be used to indirectly guide placement of a surgical device within the patient during the surgical procedure.

However, one of the concerns arising from the increased use of fluoroscopic radiation systems in medical procedures is the amount of radiation exposure to both medical staff and patients. Epidemiological data suggest that exposure to as "little" as 5 to 10 rem over a lifetime increases the risk of developing cancer. Literature also suggests that there is no lower threshold on the amount of radiation that could be considered acceptable. Further, studies have shown that elevated radiation exposure levels can be expected when larger body parts of a patient are imaged, or when parts of the medical staff's body, such as extremities, are positioned closer to the x-ray source or in the direct x-ray field.

While the exposure levels capable of producing damage to tissue are being debated and continually revised as more information is established, the cumulative effects of consistent radiation exposure remain unknown. That is, while the selected dose of radiation used in any one imaging sequence may normally be well below safe exposure limits, repeated exposure to medical staff and patients from one or more radiation sequences in procedures involving one or more patients may increase the risk of exposure for the medical staff and patients beyond what is normally considered safe operating procedures. This is possibly due to an increase in cumulative radiation dosage beyond what is normally considered safe. Recent investigations in medical diagnostics practices suggest that the dose and exposure should follow the "As Low As Reasonable" approach.

For instance, members of the surgical team may be exposed unnecessarily to x-rays when performing surgery on a patient involving the use of fluoroscopic imaging techniques. As an example, in diagnostic procedures using x-rays or computed tomography (CT) scans, a radiologist may have to hold a patient such as an infant, or an animal in the case of veterinary work, to restrain the movement of the patient in order to obtain satisfactory image resolution. In these cases, at a minimum, the hands of the radiologist or other medical staff may be exposed to harmful radiation, such as x-rays. Additionally, repeated exposure across multiple procedures on one or more patients may also increase the risk of radiation exposure to the medical staff.

The patient may also be exposed to increased risk as x-rays are used increasingly in more common doctor/patient settings. For example, mobile C-arm image intensifiers, as fluoroscopic imaging systems, are increasingly used in operating rooms, outpatient clinics, and emergency departments to image larger, denser body areas such as the pelvis or spine. The images are taken during elective and non-elective surgical procedures and may expose non-targeted bones and muscles to increased radiation, as well as other more radiosensitive underlying visceral organs. Further, the same patient may be subject to multiple exposures over his or her life-time, thereby accumulating the dose and increasing the risks of harm to the patient.

As one solution, when possible lead aprons are used to protect both medical staff and patients from such radiation. These lead aprons are effective in blocking radiation incident to one side of the apron from going through the apron and exiting the other side, and as such protect whatever is underneath the apron from radiation. For instance, when imaging a targeted body part of a patient, one or more lead aprons may be arranged around the patient allowing exposure of the targeted body part, but at the same time minimizing radiation exposure of non-targeted body parts. Also, medical staff may wear lead aprons to protect themselves from radiation when the patient is subjected to fluoroscopic imaging.

However, these lead aprons can be heavy. Because this heaviness restricts movement of arms and hands of the medical staff, lead aprons worn by the medical staff typically leave the arms and hands free in order to perform the surgical procedure. As such, these lead aprons offer limited protection to the medical staff since their hands are exposed to repeated exposure.

Moreover, gloves containing lead compounds or other metals do not provide a satisfactory solution for reducing exposure to the hands and are not typically worn by the medical staff. These gloves may be inflexible or at increased risk for tearing. As a result, the lack of protection for the arms and hands of medical staff in repeated procedures may result in a cumulative radiation exposure that is above acceptable levels.

For instance, these gloves are made of a flexible polymer containing lead or lead compounds. They also may contain a layer of lead or lead compounds made by dipping the inner surface of a flexible glove into a mixture containing lead. These leaded gloves are suitable for blocking radiation. An alternative to lead are other heavy metals or heavy metal compounds comprising cadmium, tungsten and the like. However, these lead compounds and other heavy metal compounds are known to be toxic to human tissue. As such, gloves containing these lead compounds and other heavy metal compounds could leave trace amounts on the patient's skin or on the skin of the physician, just from the ordinary use of the glove. Moreover, the addition of lead or other heavy metal compounds of sufficient concentrations into the glove to block radiation may compromise the tear resistance of the glove. When the glove tears, these lead compounds or other heavy metal compounds within the glove may be exposed to the patient. In both of these cases, the use of these gloves may potentially result in the undesired assimilation of lead or other heavy metal compounds into the bodies of patients and medical staff.

Further, gloves infused with sufficient concentrations of lead to block radiation may be inflexible or stiff. This inflexibility restricts the agile movement of the physician's hand that is necessary for delicate procedures. That is, these gloves cause the physician's fingers to lose their dexterity. Moreover, this inflexibility of the gloves reduces the tactile sensation of the hands and fingers of the person wearing the glove. Physicians rely on this tactile sensation as a secondary source of information while simultaneously viewing the fluoroscopic viewing screen. For instance, tactile sensation is used by the physician to help guide their hands and fingers when they may be inside the patient and hidden from direct view.

Thus, a need exists to exercise caution and limit exposure to radiation for both medical staff and patients. It is also desirable to protect medical staff members from radiation in a way that does not limit them from conducting their procedures.

SUMMARY OF THE INVENTION

Embodiments of the present invention relate to a shield for radiation attenuation. The shield includes an organic or an inorganic carrier suitable for topical application on human tissue, such as skin. The carrier includes an active ingredient that is homogenously dispersed throughout the carrier. The active ingredient includes an inorganic compound suitable for attenuating radiation and having an element with a high atomic number. In particular, the shield includes topically applied creams including but not limited to, pastes, gels, solutions, suspensions, or liquids that are suitable for protecting human tissue against the damaging effects of x-ray radiation. These creams may be used by medical staff and patients to protect themselves from overexposure to radiation during medical diagnostics and treatments when performing fluoroscopic or other radiation imaging of the patient.

BRIEF DESCRIPTION OF THE DRAWINGS

Exemplary embodiments are illustrated in referenced figures of the drawings which illustrate what is regarded as the preferred embodiments presently contemplated. It is intended that the embodiments and figures disclosed herein are to be considered illustrative rather than limiting.

DETAILED DESCRIPTION OF THE PREFERRED EMBODIMENTS

Reference will now be made in more detail to the preferred embodiments of the present invention, a medium for shielding patients and medical staff including surgeons, physicians, and clinicians from radiation, and a method for implementing the medium. While the invention will be described in conjunction with the preferred embodiments, it will be understood that they are not intended to limit the invention to these embodiments. On the contrary, the invention is intended to cover alternatives, modifications and equivalents which may be included within the spirit and scope of the invention.

Accordingly, embodiments of the present invention provide for a topically applicable medium having an active ingredient suitable for attenuating and/or absorbing harmful x-ray radiation. Use of these topically applicable mediums provide radiation protection for parts of the body of a member of the medical staff or patients that are normally exposed to radiation during the use of fluoroscopic imaging systems. In addition, other embodiments of the present invention provide for the above advantages and also allow for full dexterity of the hands and fingers of medical staff members for use during medical procedures. Further advantages of the embodiments of the present invention include providing radiation protection during medical procedures, without any image distortion or artifacts associated with the use of metallic shielding materials. Also, other embodiments of the present invention provide for the above advantages and also provide for tactile sensation of the hands and fingers of medical staff members during medical procedures.

Figure 1:
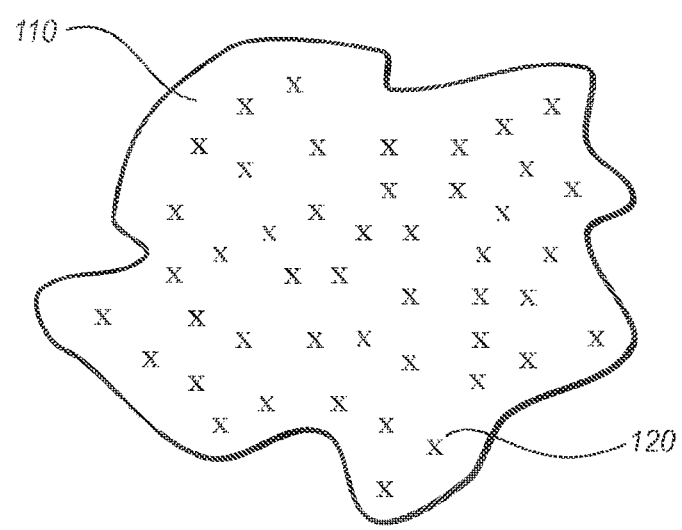
FIG. 1 is a diagram illustrating a medium that is suitable for topical application on skin that includes an active ingredient capable of attenuating radiation, in accordance with one embodiment of the present invention.

FIG. 1 is an illustration of a shield 100 for radiation attenuation, in accordance with one embodiment of the present invention. FIG. 1 is a two-dimensional depiction of the shield 100. The shield 100 includes an organic or inorganic carrier 110 that is suitable for topical application on human tissue, such as skin. The shield 100 also includes an active ingredient 120 that is homogeneously dispersed throughout the organic carrier. More specifically, the active ingredient 120 includes an element having a high atomic number and that is suitable for attenuating radiation.

The organic or inorganic carrier 110 is of a form capable of aqueous dispersion and formulated for ready and effective application on human tissue, such as skin. For instance, the carrier is of a cream composition and exhibits thixotropic characteristics, in one embodiment. That is, the cream initially resists flow when a shear stress is applied, but with sufficient force flows to form a smooth, continuous film on the skin. In one embodiment, the cream composition includes a solid content on the order of 33-50 percent and a pH ranging from 5.0 to 6.5, and are characteristic of ingredients commonly used in creams used in skin care or hand lotions.

The cream composition is in the form of an alcohol based gel, in another embodiment. The gel can be formulated using a variety of cosmetically/dermatologically acceptable vehicles, diluents, or carriers. As a characteristic, these gel compositions liquefy or freely flow from a solid state when subjected to force or vibration. These alcohol based gel compositions can be fast drying and non-greasy, or could consist of oil-in-water emulsions. As examples, alcohol based compositions can include film-forming organic polymers, such as Dermacryl.R™. LT, that impart waterproofing characteristics and decreased rub-off of the active ingredients present in the cream composition.

In still another embodiment, the organic or inorganic carrier 110 could be in a form that is capable of being sprayed. For instance, the organic carrier 110 is composed of any compound that exists in a fluid, liquid, or any appropriate state, and that is capable of being dispersed as a vapor or a fine particulate. The use of the spray implementation allows for quick application of the shield to larger areas requiring radiation protection.

As shown in FIG. 1, the shield 100 includes an active ingredient 120 that is suitable for attenuating radiation, in accordance with one embodiment of the present invention. The active ingredient is represented by the "x" symbols, and are homogeneously dispersed throughout the carrier 110, in one implementation. More particularly, the active ingredient 120 exhibits radiation attenuating capabilities. That is, the active ingredient 120 is capable of performing one or a combination of blocking, absorbing, scattering, or reflecting of x-ray radiation.

In embodiments, the active ingredient consists of any inorganic salt compound that is suitable for attenuating x-ray radiation, and that exhibits one or more of the following characteristics: non-toxic to human tissue, stable, non-flammable, free flowing, having particles with high surface area, and is capable of being well dispersed uniformly. In particular, the active ingredient 120 is comprised of an inorganic salt compound with at least one element of high atomic number. That is, the inorganic salt compound includes cations with atomic numbers high enough to effectively block x-ray radiation. More specifically, the active ingredient is composed of any element, compound, or combination of compounds which contains a cation of high atomic number, such that it is capable of effectively attenuating x-ray radiation emanating from fluoroscopic imaging systems and other medical diagnostics and treatment systems.

In one embodiment, the active ingredient includes an element taken from the group consisting of bismuth, barium, and lanthanum. For instance, the element forms the cation in the organic salt compound.

In one embodiment, the active ingredient is a barium salt. For instance, the barium salt compound is barium sulfate (e.g., $Ba_2SO_4$). Barium sulfate has been proven to be safe and non-toxic to humans. In another embodiment, the active ingredient is a lanthanum salt. For instance, the lanthanum salt compound is lanthanum oxide (e.g., $La_2O_3$). In still another embodiment, the active ingredient is a bismuth salt. For instance, the bismuth salt compound is bismuth oxide (e.g., $Bi_2O_3$). In still another embodiment, the active ingredient is a combination of barium sulfate, bismuth oxide, and lanthanum oxide of varying ratios from 0 to 100. That is, each of the compounds may be varied from 0 to 100 in a composition making up the active ingredient.

In still other embodiments, the active ingredient composed of organic agents are contemplated. The organic agents are also suitable for attenuating radiation.

In one embodiment, the active ingredient comprises at least 25 percent by weight of the composition forming the shield 100, which includes the carrier 110 and the active ingredient 120. In other more specific embodiments, the active ingredient ranges between 33-50 percent by weight of the composition forming the shield 100. In another embodiment, the active ingredient ranges between 1-20 parts by weight of a composition forming the shield 100, which includes a composition comprising the carrier and the active ingredient, wherein the carrier approximates 1 part by weight of the composition. In other embodiments, the active ingredient comprises at least 10 percent by volume of a composition comprising the carrier and the active ingredient. In another embodiment, the active ingredient comprises 10-67 percent by volume of the composition. In still another embodiment, the carrier ranges between 0.1 to 99.9 percent by weight of the composition comprising the carrier 110 and the active ingredient 120, and where the active ingredient comprises the remaining portion by weight of the composition. In each of these embodiments, the active ingredient has a radiation attenuating capacity that sufficiently protects against radiation exposure. The level of protection is achieved while preserving dexterity of the hands and fingers and maintaining tactile sensation of the hands and fingers. As such, the level of protection is achieved without comprising the execution of clinical techniques and without deleteriously influencing the outcome of such clinical techniques.

In combination, the shield 100 composition, comprising cream based compositions and an active ingredient, is formulated to provide radiation protection, in embodiments of the present invention. The cream based composition of the shield 100 comprises a cosmetically acceptable vehicle, carrier, or diluent and exhibits characteristics including an aqueous, dispersed phase, and an oily, dispersed phase. The active ingredient consists of one or more non-toxic United States Food & Drug Administration (FDA) approved radiation attenuating compounds, of various concentrations, and is capable of providing protection from harmful x-ray radiation.

In one specific implementation, the shield 100 consists of cream based compositions blended with an active ingredient that may be in powder form. For instance, the active ingredient includes an inorganic radiation absorbing salt in powder form, such as barium sulfate, lanthanum oxide, bismuth oxide, or a combination therein. To form the shield 100, the active ingredient is blended homogeneously with a base containing the carriers to form a topically applied radiation protection cream composition that provides substantial attenuation of radiation.

In still other embodiments, the compound or compounds forming the active ingredient are selected as a function of the desired radiation protection factor. The radiation protection factor may be expressed mathematically by the degree of attenuation of x-ray radiation in comparison to a known standard, such as those existing for metal foils (e.g., aluminum). As such, the compound or compounds forming the active ingredient may consist of varying concentrations in order to increase or decrease the effectiveness of radiation attenuation. For instance, the percent by weight of the active ingredient may be increased or decreased to obtain the proper radiation protection factor.

In addition to or separate from the above variation in concentration, compounds may be selected based on their ability in combination to increase or decrease the effectiveness of radiation attenuation. For instance, the active ingredient may include a barium salt compound and a bismuth salt compound. In general, the bismuth salt compound, partly due to its higher atomic number, exhibits higher radiation attenuating capacity than a barium salt compound. As such, concentrations of the bismuth salt compound may be varied in relation to the barium salt compound to achieve the proper radiation protection factor.

Figure 2A:
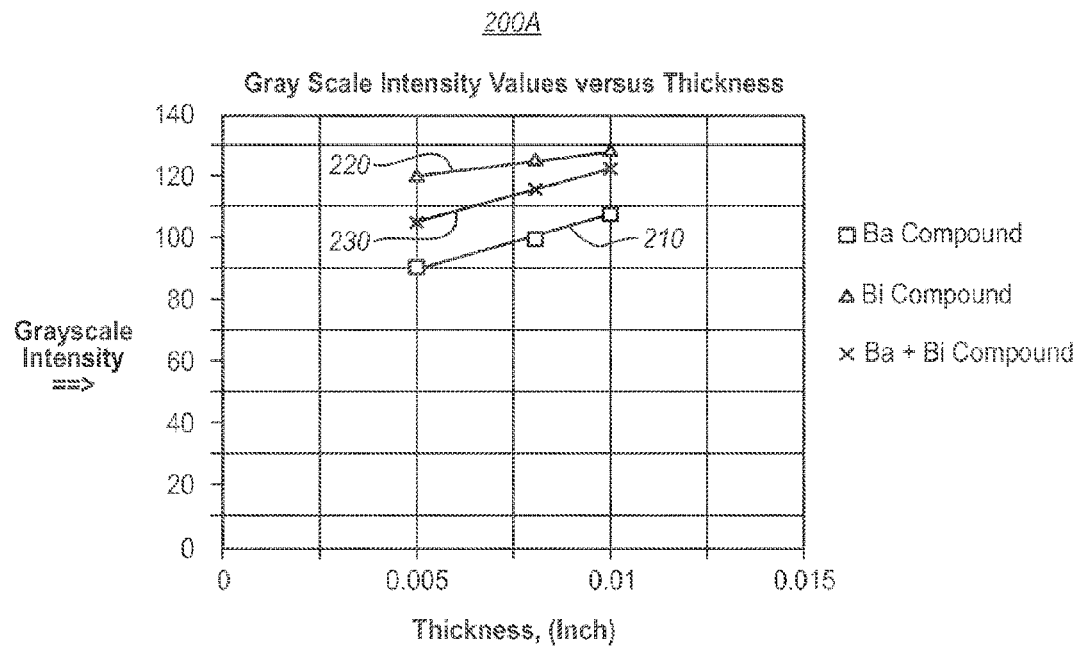
FIG. 2A is a graph illustrating the gray scale intensity versus thickness of various compounds, in accordance with one embodiment of the present invention.
Figure 2B:
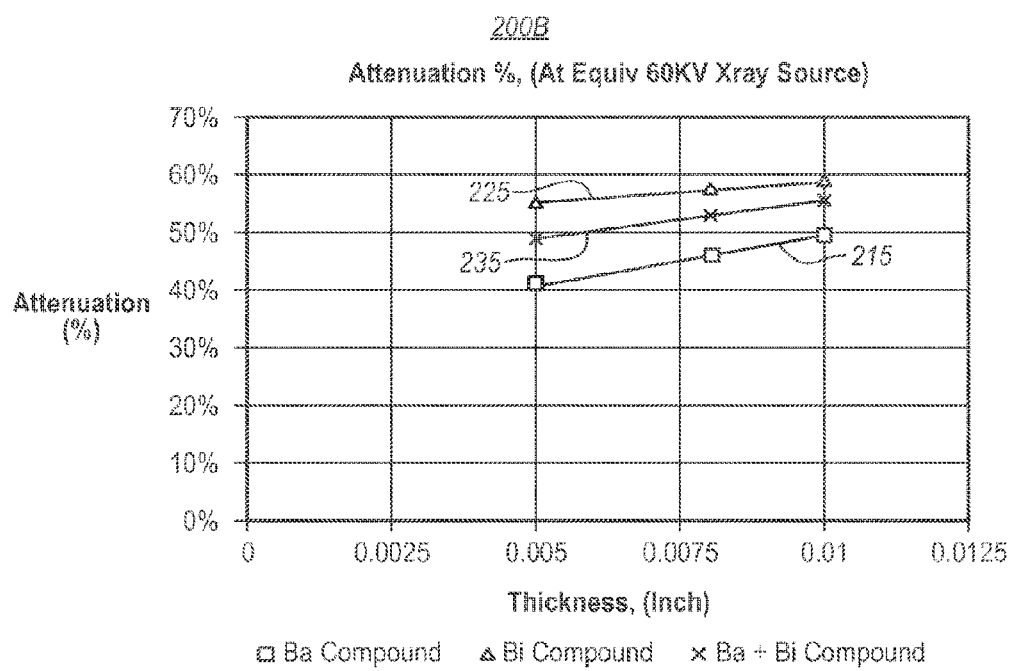
FIG. 2B is a graph illustrating the radiation attenuation abilities of various compounds, in accordance with one embodiment of the present invention.

FIGS. 2A and 2B are graphs illustrating experimental results for various shield compositions. For instance, these various shield compositions include active ingredients of barium sulfate, bismuth oxide, and a homogenous mixture of barium sulfate and bismuth oxide. Where it is a mixture, the active ingredient is formulated in a 50:50 atomic number proportion of barium to bismuth.

Each of the various active ingredients is ground into a fine homogeneous powder form and blended with a carrier common to each of the shield compositions. As an example and for purposes of experimentation, the carrier formulation includes glycerin, stearic acid, glycol stearate, glycerin stearate, and carbomer in an aqueous mixture. The fine powders of active ingredients were mixed with the carrier in a weight ratio ranging from 5.5 to 8 parts by weight of the powder to 1 part by weight of the carrier composition. The powders were blended homogeneously to obtain a smooth, homogeneous creamy texture typically used for topical applications such as cosmetic skin moisturizing creams or creams used for protection from solar ultra-violet radiation such as sun-block creams.

As such, three different shield cream based compositions as described above were formulated and tested, as indicated above. Each of the prepared creams were applied onto a polymer test film with the creams having three controlled thicknesses: 0.005 inch, 0.08 inch, and 0.010 inch. The test films were then placed in a Faxitron x-ray cabinet, and exposed to an x-ray source excited at 18 kV for 120 seconds. As a control, an aluminum step wedge with steps of 0.003 inch, 0.006 inch, and 0.009 inch was also simultaneously exposed to the x-ray source and used to calibrate the x-ray absorption of the test films.

Upon exposure to the radiation from the x-ray source, the test films were developed, and the resulting images indicated various degrees of radiation attenuation from the creams of controlled composition and thicknesses. The images from the test films were analyzed and compared to the images provided from the aluminum step wedge. More specifically, when examining the test films, areas of the images showing higher levels of x-ray attenuation appear in lighter gray contrast. Conversely, areas of the images showing lower levels of x-ray attenuation appear as darker gray contrast. In summary, the higher the attenuation of radiation due to the applied creams thickness and composition, the lighter the gray contrast appears on the corresponding image.

FIG. 2A is a graph illustrating the gray scale intensity versus thickness of the three shield cream based compositions tested, in accordance with one embodiment of the present invention. In particular, the line 210 corresponds to a cream based composition including barium sulfate ($Ba_2SO_4$) of varying thicknesses. Also, line 220 corresponds to a cream based composition including bismuth oxide ($Bi_2O_3$) of varying thicknesses. Further, line 230 corresponds to a cream based composition including a homogenous mixture of barium sulfate ($Ba_2SO_4$) and bismuth oxide ($Bi_2O_3$).

For each of the cream based compositions, gray scale intensity was quantified and calibrated against the gray scale intensity values from the aluminum step wedge control. As shown in FIG. 2A, the composition including barium sulfate ($Ba_2SO_4$) corresponding to line 210 provided the lowest gray scale intensity values for each of the thicknesses tested. In other words, these values corresponded to the darkest gray scale contrast. The composition including a homogenous mixture of barium sulfate ($Ba_2SO_4$) and bismuth oxide ($Bi_2O_3$) corresponding to line 230 provided more gray scale intensity values, when compared to the composition including barium sulfate ($Ba_2SO_4$). These values corresponding to line 230 were due to a lighter gray scale contrast compared to those corresponding to line 210. And the composition including bismuth oxide ($Bi_2O_3$) corresponding to line 220 provided the highest gray scale intensity values of the three compositions tested, corresponding to the highest gray scale contrast.

FIG. 2B is a graph illustrating the radiation attenuation abilities of the various cream based compositions that were tested, and are based on the gray scale intensity values from FIG. 2A, in accordance with one embodiment of the present invention. In particular, the gray scale values from FIG. 2A were translated into an equivalent radiation attenuation percentage and adjusted to reflect values based on a 60 kV x-ray source that is typically used in clinical settings. In particular, the line 215 corresponds to the radiation attenuation readings for the cream based composition including barium sulfate ($Ba_2SO_4$) of varying thicknesses. Also, line 225 corresponds to the radiation attenuation readings for the cream based composition including bismuth oxide ($Bi_2O_3$) of varying thicknesses. Further, line 235 corresponds to radiation attenuation readings a cream based composition including a homogenous mixture of barium sulfate ($Ba_2SO_4$) and bismuth oxide ($Bi_2O_3$).

As expected, the values shown in FIG. 2B reflect the performance of each of the compositions in terms of gray scale intensity from FIG. 2A. That is, as shown in FIG. 2B, the composition including bismuth oxide ($Bi_2O_3$) corresponding to line 225, provided the highest attenuation of radiation for each of the thicknesses tested. The composition including the homogenous mixture of barium sulfate ($Ba_2SO_4$) and bismuth oxide ($Bi_2O_3$) corresponding to line 235 provided lesser radiation attenuation, when compared to the composition including bismuth oxide ($Bi_2O_3$). And the composition including barium sulfate ($Ba_2SO_4$) corresponding to line 215 provided the least attenuation of radiation of the three compositions tested.

More particularly, as shown in FIG. 2B, each of the cream based compositions were successful in attenuating a significant amount of x-ray radiation. For instance, the composition including barium sulfate ($Ba_2SO_4$) corresponding to line 215 provided attenuation values as a percentage between 40 and 50 percent. The composition including the homogenous mixture of barium sulfate ($Ba_2SO_4$) and bismuth oxide ($Bi_2O_3$) corresponding to line 235 provided attenuation values as a percentage between 50 and 60 percent. And the composition including bismuth oxide ($Bi_2O_3$) corresponding to line 225 provided the attenuation values as a percentage between 55 and 60 percent.

In still another embodiment, the active ingredient capable of blocking radiation is infused directly into a fabric layer comprising a drape, or is infused into a layer that is adjacent to a substrate layer comprising the drape. More specifically, the inorganic radiation protective salt compounds can be impregnated into or onto natural or synthetic, woven or non woven fiber based disposable paper or cloth products, in accordance with one embodiment of the present invention. It is contemplated that the radiation protecting drapes are hermetically sealed for sterility and ease of use during medical procedures.

Figure 3:
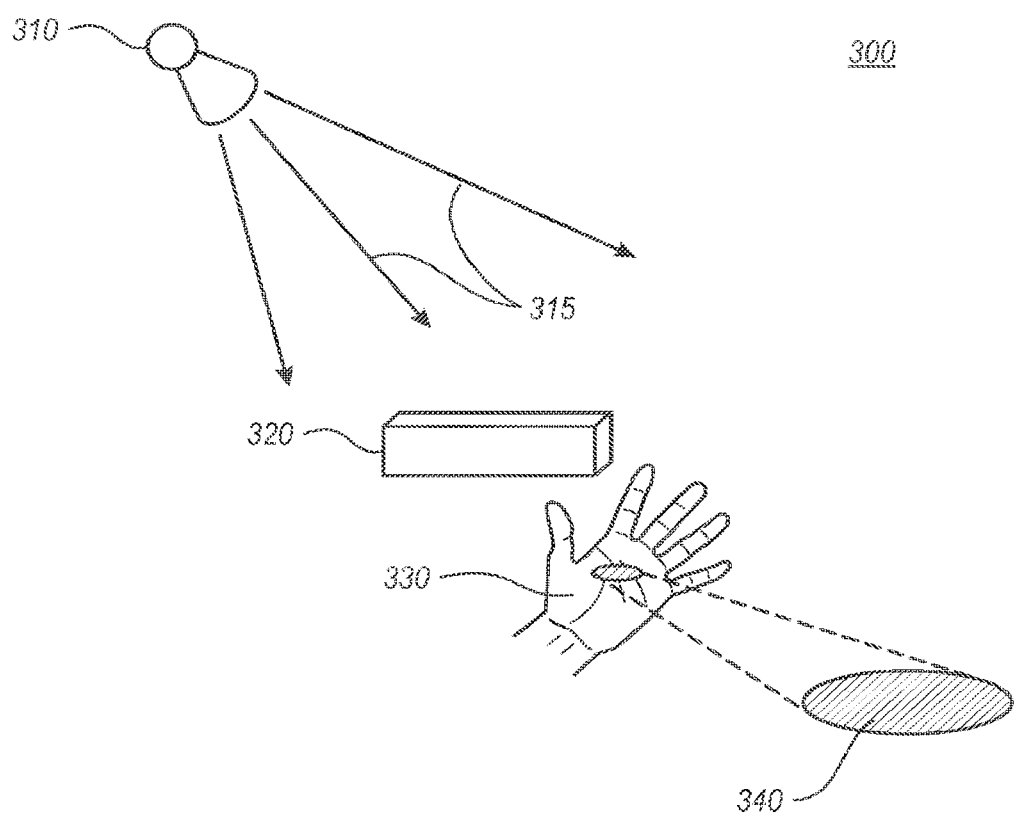
FIG. 3 is a system capable of radiation attenuation, in accordance with one embodiment of the present invention.

FIG. 3 is a system 300 capable of radiation attenuation, in accordance with one embodiment of the present invention. The system is capable of being implemented in any medical setting implementing fluoroscopic imaging or other medical diagnostic or treatment systems that employ radiation for use in diagnostic detection, treatment, or guiding purposes when performing medical procedures. In particular, system 300 is capable of providing radiation protection to arms and hands of medical staff.

System 300 includes a radiation source 310 emitting radiation over a radiation field 315. A targeted specimen 320, such as the targeted body part of a patient, is located within the radiation field 315. For instance, the specimen may be located on a raised platform or table for available access. For purposes of illustration, specimen 320 is illustrated as a three-dimensional box, and represents any type of specimen, such as an arm, abdomen, leg, or any other body part of a human or non-human patient.

For example, the radiation source is a fluoroscopic radiation system used for imaging a targeted specimen 320, such as the targeted body part of a patient. As a practical example, mobile C-arm fluoroscopic imaging systems are commonly used in in-patient and out-patient settings. As such, this C-arm imaging system includes the radiation source 310 and is used for imaging the specimen when performing medical procedures.

As shown in FIG. 3, the radiation field 315 completely surrounds the specimen and even spreads into areas beyond where the specimen is located. A non-targeted body part many times is located within the radiation field 315, where the body part is not targeted for imaging, but is exposed to radiation. For instance, hand 330 is a body part that is located within the radiation field 315 and is exposed to x-ray radiation from the radiation source 310. In some instances, the hand as the non-targeted body part is associated with the specimen. For instance, the hand 330 may be part of the patient. In other instance, the hand as the non-targeted body part may be part of a member of the medical staff, where the hand is used to stabilize the specimen or to hold surgical instruments engaged with the patient when performing medical procedures. Without proper protection, the hand 330 is at risk for overexposure to the radiation from the radiation source 310 while the specimen is being imaged.

As a solution, system 300 also includes a radiation shield 340 that is topically applied to human tissue of the body part, and may be advantageously placed between the radiation source 310 and the body part 320. As shown in FIG. 3, the radiation shield 340 is topically applied to the skin of the hand 330. This shield may be applied to a portion of the hand 330 or the entire hand 330 as required. More particularly, the radiation shield 340 is suitable for attenuating radiation from the radiation source 310.

The radiation shield 340 comprises a carrier (e.g., organic or inorganic) having thixotropic properties, in one embodiment. For instance, the carrier is a cream based organic composition that is formulated for ready and effective application on the skin. The radiation shield 340 also includes an active ingredient that is homogeneously dispersed throughout the carrier. More particularly, the active ingredient comprises an inorganic salt compound having an element having a high atomic number, and is suitable for attenuating radiation. For instance, in embodiments, the inorganic salt compound is taken from one of the following: barium sulfate, bismuth oxide, lanthanum oxide, or a combination therein.

In another embodiment, the fluoroscopic radiation system outputs essentially monochromatic radiation. That is, the radiation in the radiation field 315 is essentially of a single frequency. As such, the active ingredient in the radiation shield 340 is specifically configured to attenuate the monochromatic radiation emanating from the radiation source 310.

The system 300 also includes a drape for radiation attenuation, in accordance with one embodiment of the present invention. The drape is suitable for covering other body parts at risk for overexposure to radiation from the radiation source. The drape can cover the patient, or may be used by medical staff. The drape comprises a flexible substrate, such as that made from a flexible fabric. The drape also includes a layer adjacent the flexible substrate, wherein the layer comprises a composition homogeneously dispersed throughout the layer, and is similar to or includes the active ingredient previously described for use in the radiation shield 340.

In still another embodiment, a system includes a radiation source, targeted specimen, and a non-targeted body part, previously described in FIG. 3. In addition, the system includes a drape for radiation attenuation. The drape is suitable for covering the body part. The drape comprises a flexible substrate. In addition, the drape includes a layer adjacent the flexible substrate, wherein the layer includes a composition homogeneously dispersed throughout the layer that includes the active ingredient previously described for use in the radiation shield 340. In still another implementation, the drape includes the active ingredient homogenously dispersed throughout the flexible substrate, such that the active ingredient is incorporated within the flexible substrate.

In still another embodiment, a system includes a radiation source, targeted specimen, and a non-targeted body part, previously described in FIG. 3. In addition, the system includes a radiation shield that is topically applied to human tissue of the non-targeted body-part. The radiation shield is suitable for attenuating radiation from the radiation source. More specifically, the radiation shield includes a carrier (e.g., organic based or inorganic based carriers), and an active ingredient that is homogeneously dispersed throughout the carrier. The active ingredient comprises an inorganic salt compound with at least one element having a high atomic number and is suitable for attenuating radiation. Also, a composition comprising the carrier and the active ingredient is in a form capable of being sprayed.

Figure 4:
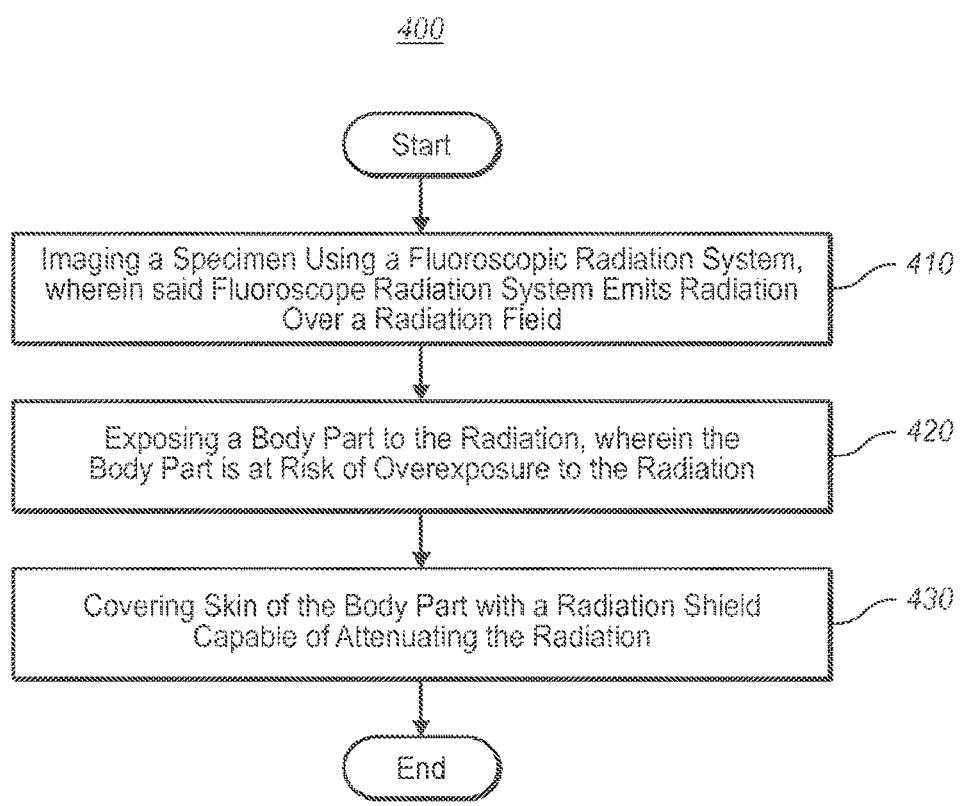
FIG. 4 is a flow diagram illustrating a method for shielding radiation, in accordance with one embodiment of the present invention.

FIG. 4 is a flow diagram 400 illustrating a method for providing radiation attenuation. The method of the flow diagram 400 is capable of being implemented in any medical setting in which fluoroscopic imaging systems and other medical diagnostics and treatment systems used for diagnostic detection, treatment, or guiding purposes when performing medical procedures. In particular, the method of flow diagram 400 is capable of providing radiation protection to arms and hands of medical staff.

At 410, a specimen is imaged using a fluoroscopic radiation system. The fluoroscopic radiation system emits x-ray radiation over a radiation field. The specimen is located within the radiation field, and may be viewed using a fluoroscopic viewing screen.

At 420, a body part is exposed to the radiation. The body part is not targeted for imaging, and is at risk of radiation exposure. The body part may belong to the patient, or it may belong to a member of the medical staff performing the medical procedure on the patient. For instance, the body part may be a hand or arm of the physician performing the medical procedure.

At 430, human tissue (e.g., skin) of the non-targeted body part is covered with a radiation shield that is capable of attenuating the radiation. More particularly, the radiation shield is topically applied to the human tissue. For purposes of clarification, it is understood that the radiation shield is applied beneficially to protect against over-exposure to radiation, and that in one implementation the radiation shield is applied before there is any risk of radiation exposure, and in another implementation the radiation shield is applied while being exposed to radiation. In one implementation, the radiation shield comprises a carrier having thixotropic properties. For instance, the carrier is a cream based organic composition that is formulated for ready and effective application on the skin. In another embodiment, the carrier is in a form that is capable of being sprayed or in a form that can be wrapped around the skin. In either instance, the radiation shield 340 also includes an active ingredient that is homogeneously dispersed throughout the carrier.

More particularly, the active ingredient comprises an inorganic salt compound having a high atomic number, and is suitable for attenuating radiation.

In another embodiment, a protective covering is placed over the human tissue. For instance, the protective covering may cover skin of fingers of a hand of a member of the medical staff. During some medical procedures, a double layer of protective covering is placed over the human tissue. For instance, the hand may be double-gloved to provide additional protection to the hand.

A medium capable of topical application to human tissue and that is capable of attenuating radiation attenuation is thus described. While the invention has been illustrated and described by means of specific embodiments, it is to be understood that numerous changes and modifications may be made therein without departing from the spirit and scope of the invention as defined in the appended claims and equivalents thereof. Furthermore, while the present invention has been described in particular embodiments, it should be appreciated that the present invention should not be construed as limited by such embodiments, but rather construed according to the below claims.

I claim:

1. A method of attenuating x-ray radiation, comprising:
    topically applying a cream composition suitable for attenuating x-ray radiation onto a part of a body, the cream composition comprising bismuth oxide, wherein the amount of bismuth oxide is effective to attenuate x-ray radiation;
    spreading the cream composition over the part of the body; and
    exposing the part of the body to x-ray radiation being emitted from a radiation source.

2. The method of claim 1, wherein the cream composition comprises an aqueous mixture.

3. The method of claim 1, wherein the cream composition comprises an emulsion.

4. The method of claim 1, wherein the cream composition comprises at least one of a paste, a gel, a solution, a suspension, or a liquid.

5. A method of attenuating x-ray radiation, comprising:
    topically applying a cream composition suitable for attenuating x-ray radiation over a part of a body, the cream composition comprising a carrier and an active ingredient that is dispersed throughout the carrier, wherein the active ingredient comprises bismuth oxide, wherein the amount of bismuth oxide is effective to attenuate x-ray radiation; and
    exposing the part of the body to x-ray radiation being emitted from a radiation source.

6. The method of claim 5, wherein the part comprises at least one of a hand or an arm.

7. The method of claim 5, wherein the cream composition is topically applied onto human tissue.

8. The method of claim 5, wherein the radiation source comprises a fluoroscopic radiation system.

9. The method of claim 5, wherein the carrier comprises an inorganic carrier.

10. The method of claim 5, wherein the carrier comprises an organic carrier.

11. The method of claim 5, wherein the cream composition comprises an aqueous mixture.

12. The method of claim 5, wherein the cream composition comprises an emulsion.

13. The method of claim 5, wherein the cream composition comprises at least one of a paste, a gel, a solution, a suspension, or a liquid.

14. The method of claim 5, wherein the active ingredient is a ground powder.

15. The method of claim 5, wherein the cream composition comprises between 1 and 20 parts by weight of active ingredient.

16. The method of claim 5, wherein the cream composition comprises between 10% and 67% by volume of active ingredient.

17. The method of claim 5, wherein the active ingredient is configured to attenuate x-ray radiation by one or more of blocking, absorbing, scattering, or reflecting x-ray radiation.

* * * * *